United States Patent [19]
Kupfer et al.

[11] Patent Number: 5,854,240
[45] Date of Patent: Dec. 29, 1998

[54] METHYLENE BLUE FOR THE TREATMENT OR PROPHYLAXIS OF ENCEPHALOPATHY CAUSED BY IFOSFAMIDE

[75] Inventors: Adrian Kupfer, Herzogenbuchsee; Thomas Cerny, Bern, both of Switzerland

[73] Assignee: Newcastle University Ventures Limited, Newcastle, United Kingdom

[21] Appl. No.: 646,292

[22] PCT Filed: Nov. 14, 1994

[86] PCT No.: PCT/GB94/02494

§ 371 Date: Oct. 18, 1996

§ 102(e) Date: Oct. 18, 1996

[87] PCT Pub. No.: WO95/13079

PCT Pub. Date: May 18, 1995

[30] Foreign Application Priority Data

Nov. 12, 1993 [GB] United Kingdom .................... 9323399

[51] Int. Cl.⁶ ............................ A61K 31/54; A61K 31/66

[52] U.S. Cl. .......................................... 514/224.8; 514/110

[58] Field of Search .................................. 514/110, 224.8

[56] References Cited

FOREIGN PATENT DOCUMENTS 1188159  4/1970  United Kingdom .
8604679  12/1984  WIPO .

OTHER PUBLICATIONS

The Merck Index, 11th Ed, p. 778, No. 4822, 1989.
Dyer, An Index of Tumor Chemotherapy, pp. 10–12 and 128, 1949.

Primary Examiner—Jerome D. Goldberg
Attorney, Agent, or Firm—Hale and Dorr LLP

[57] ABSTRACT

The encephalopathy caused by ifosfamide and similarly acting compounds can be prevented or treated by the administration of methylene blue or another compound which is able to oxidize a reduced flavin moiety. Pyritinol is able to reduce other aspects of ifosfamide toxicity.

7 Claims, 4 Drawing Sheets

METHYLENE BLUE FOR THE TREATMENT OR PROPHYLAXIS OF ENCEPHALOPATHY CAUSED BY IFOSFAMIDE

FIELD OF THE INVENTION

This invention relates to pharmaceutical uses of compounds and to pharmaceutical compositions. In particular, the invention relates to the treatment or prophylaxis of encephalopathy, as may be caused by certain phosphoramide compounds.

BACKGROUND OF THE INVENTION

Ifosfamide (N,3-bis(2-chloroethyl)tetrahydro-2H-1,3,2-oxazaphosphorin-2-amine 2-oxide)

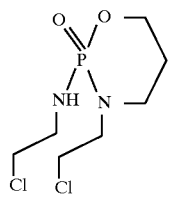

is a phosphoramide compound which is a well known antineoplastic drug. It is a structural isomer of cyclophosphamide (N,N-bis(2-chloroethyl)tetrahydro-2H-1,3,2-oxazaphosphorin-2-amine 2-oxide)

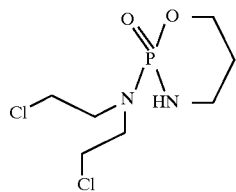

which is also a phosphoramide compound and has a similar clinical utility. Although the antineoplastic activities of ifosfamide and cyclophosphamide are similar, there are sufficient differences for ifosfamide to be useful in situations which have proved refractory to cyclophosphamide therapy.

Ifosfamide is strictly speaking a pro-drug: it has to be metabolised in the liver to be active. In view of this, orally administered ifosfamide would be expected to be more active than the parenterally administered compound; and indeed it is. Oral administration of ifosfamide is desirable not only for the clinical reason of improved bio-activity of the drug but also for the economic reason that non-parenteral administration would reduce hospitalisation. Unfortunately, at least some of ifosfamide's toxic effects are also more pronounced on oral administration, again because of the effects of its metabolites. Surprisingly, until now the biochemical activities by which cyclophosphamide and in particular ifosfamide form their extremely toxic metabolites has remained illusive. It should be appreciated that the group of pharmaceuticals known as oxazaphospharines, such as ifosfamide, cyclophosphoramide and bromoifosfamide, are optically active compounds and therefore any reference made throughout this disclosure, for example, to ifosfamide, is also intended to include the R and S isomers of ifosfamide unless the context requires otherwise.

As with many effective antineoplatic drugs, the toxicity of ifosfamide is clinically a very real problem. Ifosfamide causes haemorrhagic cystitis, a severe toxicity to the bladder, (as does, to a lesser extent, cyclophosphamide) and is practically always administered in conjunction with mesna (sodium 2-mercaptoethanesulphonate), which has a uroprotective action against the effects of both ifosfamide and cyclophosphamide. Although the urinary tract toxicity can therefore now adequately be managed, the same cannot be said for other toxic effects of ifosfamide, particularly its effects on the central nervous system (CNS).

Martindale (28th Edition, 1982) reports that about 10% of patients receiving intravenous ifosfamide experience CNS side effects, especially confusion and lethargy. When ifosfamide is administered orally, the position is even worse: despite its improved efficacy against many tumour types when administered orally, the drug cannot be ethically justified for oral administration, in view of the CNS side effects. In fact, it has been reported that Asta Medica of Frankfurt, who developed ifosfamide, have ceased to sponsor clinical trials of oral formulations of the drug, largely because of the unwillingness of regulatory authorities to grant clinical trial certificates. Even when administered parenterally, the use of ifosfamide at high doses and in patients with organ dysfunction (such as renal failure) is contraindicated because of the frequent occurrence of CNS toxicity.

The CNS toxicity of ifosfamide manifests itself as encephalopathy; in other words, patients exhibit signs of cerebral irritation without any localised lesion to account for them. The cerebral irritation is apparent as cognitive, as opposed to motor or sensory dysfunction, and the symptoms experienced by patients include, in addition to the confusion and lethargy referred to above, sleep disturbance, hallucinations, psychoses and often frank coma.

To date, the only option to the clinical oncologist, if ifosfamide encephalopathy should occur has been the withdrawal of ifosfamide therapy, with the inevitable consequence for the progression or metastasis of the tumour. So there has existed for some time a need for effective means for monitoring and, especially, preventing and treating ifosfamide encephalopathy. In spite of past efforts, the mechanism of ifosfamide encephalopathy, the factors affecting it and the means for controlling it have proved illusive. Vast numbers of cancer patients who could otherwise benefit from ifosfamide chemotherapy are presently excluded from treatment.

SUMMARY OF THE INVENTION

The present invention relates to a solution to this problem. It has been discovered that toxic effects of encephalopathy-causing compounds such as ifosfamide are due to interference with one or more flavoproteins or other components of the respiratory chain. Toxicity can therefore be avoided or ameliorated by administering compounds which reduce the effect of that interference. In particular, it has been discovered that methylene blue (3,7-bis(dimethylamino)phenothiazin-5-ium chloride) and compounds which act similarly to methylene blue, including methylene blue in its reduced form: leucomethylene blue, can prevent or treat toxicity, especially encephalopathy, caused by such compounds as ifosfamide.

DETAILED DESCRIPTION

According to a first aspect of the invention, there is provided the use of a first compound in the preparation of a medicament for preventing or treating toxicity caused by a second compound, wherein the first compound is able to oxidise a reduced flavin moiety and wherein the second compound is ifosfamide or another compound which causes toxicity in a manner similar to ifosfamide. The invention therefore has application in a method of treating or preventing toxicity caused by ifosfamide or another compound which causes toxicity in a manner similar to ifosfamide, the method comprising administering to a subject an effective amount of a compound which is able to oxidise a reduced flavin moiety.

The compounds whose toxicity the present invention is useful in alleviating include ifosfamide and all those compounds which cause toxicity, particularly encephalopathy, in a manner similar to ifosfamide. Many such compounds are also antineoplastic or cytotoxic agents useful in cancer chemotherapy. More specifically, the invention is useful in alleviating encephalopathy caused by phosphoramide compounds. Certain of those phosphoramide compounds, including ifosfamide itself, are disclosed in GB-A-1188159 and fall within general formula I:

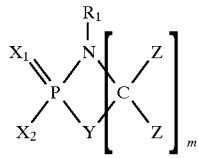

wherein $R_1$ represents $C_1$–$C_4$ alkyl substituted by one or more halogen atoms, $X_1$ represents an oxygen or sulphur atom, Y represents an oxygen atom or a group of the formula —NH— or —$NZ_1$— in which $Z_1$ represents $C_1$–$C_4$ alkyl optionally substituted by one or more halogen atoms or hydroxy groups, each Z independently represents hydrogen, halogen, $C_1$–$C_4$ alkyl, hydroxy or hydroxymethyl, m represents 2 or 3 and $X_2$ represents an ethyleneimine group or a group of the general formula Ia:

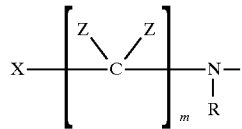

wherein R represents hydrogen or $C_1$–$C_4$ alkyl optionally substituted by one or more halogen atoms or hydroxy groups, X represents a halogen atom or hydroxy group and Z and m have the meanings given above.

Preferred alkyl groups are ethyl, and preferred halogen atoms are bromine and, especially, chlorine. When Z is not hydrogen it is preferably 2-chloroethyl or 3-chloropropyl. $X_1$ is preferably oxygen. Other preferences include those referred to in GB-A-1188159: for example, preference is given to compounds of general formula II:

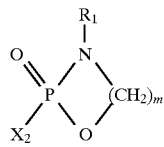

wherein $R_1$, $X_2$ and m have the same meaning as for general formula I. Most preferred are compounds of general formula III:

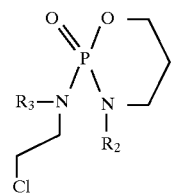

wherein $R_2$ represents a 2-chloroethyl or 3-chloropropyl group (preferably 2-chloroethyl), and $R_3$ represents hydrogen or a methyl or ethyl group, possibly substituted in the 2-position with hydroxy or, preferably, chlorine.

The invention is expected to be particularly useful in conjunction with ifosfamide therapy.

Other phosphoramide compounds which cause encephalopathy include TEPA (1,1',1"-phosphinylidynetrisaziridine) and thio-TEPA (1,1',1"-phosphinothioylidynetrisaziridine), as shown in general formula IV:

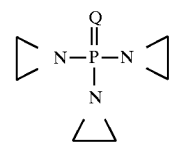

wherein Q represents oxygen for TEPA and sulphur for thio-TEPA.

Analogues of thio-TEPA having included compounds of general formula V:

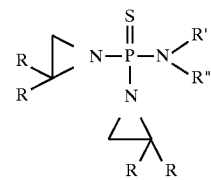

in which each R independently is hydrogen or $C_1$–$C_4$ alkyl and each of R' and R" independently is hydrogen or $C_1$–$C_4$ alkyl or, when taken together with the nitrogen atom to which they are attached, R' and R" form a saturated heterocyclic radical containing from 3 to 6 atoms.

It is believed that the encephalopathic toxicity of ifosfamide and similarly toxic compounds is due to the formation of certain haloacetic acids, particularly chloracetic acid, and certain aldehyde metabolites. For example, the 2-chloroethyl group at the 3-position of the ifosfamide ring is believed to be metabolised, probably by cytochrome P450 in the liver or elsewhere, to chloracetaldehyde ($ClCH_2CHO$), which is subsequently oxidised to chloracetic acid ($ClCH_2COOH$). Chloracetaldehyde is putatively a strong encephalopathic metabolite of ifosfamide. Chloracetic acid is also a potent acetylating and alkylating agent, with an affinity for sulphur in oxidation state II. It may also be a substrate for enzymes in the tricarboxylic acid cycle, generating highly toxic chlorocitric acid and other halogenated metabolites.

Other compounds which similarly are reactive with sulphur II include aziridine-containing compounds, that is to say compounds which contain the structure:

As well as going some way to explain the toxicity of thio-TEPA and related compounds, this observation may also play a part in explaining ifosfamide toxicity, as a 2-chloroethylamino moiety (particularly a primary 2-chloroethylamino moiety, as present in the 3-position in ifosfamide but absent in cyclophosphamide) may react to form an aziridine ring.

It is therefore possible that ifosfamide encephalopathy and similar encephalopathies can now be explained on the basis of reaction with sulphur II, or other sites, in critical enzymes or enzyme cofactors. For example, in the electron transport chain which gives rise to oxidative phosphorylation at the mitochondrial membrane, iron-sulphur centres ("non-haem iron") play a crucial role. These complexes are held in place, for instance in the flavin-containing NADH dehydrogenase complex ("Complex I"), by cysteine residues. If ifosfamide metabolites disrupt iron-sulphur centres, whether by reacting with the anchoring cysteine residues or by reacting with the sulphur in the iron-sulphur centre itself, so as to prevent or reduce the electron transport role of flavin, then the electron transport chain would become blocked and ATP generation would be severely attenuated. While the consequences of greatly reduced ATP generation are serious for the body as a whole, the consequences for the brain may be so severe as to account for the clinically observed encephalopathy.

The affinity of ifosfamide's metabolites for sulphur (II) may also deplete the cell's pool of coenzyme A (CoA), which is a thiol in its non-esterified form. As CoA is essential for supplying carbon atoms to the tricarboxylic acid cycle, and from the β-oxidation of fatty acids, both of which feed into the respiratory electron transport chain, the overall effect may be synergistic.

The invention makes use of compounds which are able to oxidise a reduced flavin moiety, for example in a flavin-containing electron transfer protein or a flavin-linked oxidation-reduction enzyme. In particular, the enzyme will usually be a flavin dehydrogenase. One of the most crucial flavin dehydrogenases is NADH dehydrogenase or, more formally, NADH-ubiquinone oxidoreductase (Complex I) in the electron transport chain. This enzyme complex accepts electrons from NADH (generated for example by glycolysis and the tricarboxylic acid cycle), thereby oxidising NADH to NAD and reducing the flavin moiety. In turn, the electrons are passed on, by means of an iron-sulphur centre, to coenzyme Q (ubiquinone) and the reduced flavin is reoxidised. Subsequently, the electrons are transported, via a second iron-sulphur centre, a complex (Complex III) comprising cytochrome b ($b_{566}$ and $b_{562}$), a third iron-sulphur centre and cytochrome $c_1$, cytochrome c and a complex (Complex IV) of cytochromes a and $a_1$ to molecular oxygen, which is reduced to water.

In this electron transport or respiratory chain, hydrogen ions (protons) are transported across the mitochondrial membrane at complex I, complex III and complex IV. The transmembrane proton-motive force established by the resulting hydrogen ion gradient drives the phosphorylation of ADP to ATP by the membrane-spanning enzyme $F_1$ ATPase.

The generation of ATP, the "loose change" of energy in the cell, is therefore dependent in aerobic organisms on the functioning of the electron transport chain. If that chain is blocked at a sufficiently early stage to prevent even the first of the three "proton pumps" operating, the cell may rapidly cease proper functioning.

Other flavoproteins involved in the electron transfer or respiratory chain include electron transfer flavoprotein (ETF) and electron transfer flavoprotein-ubiquinone oxidoreductase (ETF-QO). These proteins mediate electron transfer from mitochondrial oxidation of fatty acids and various amino acids as well as the catabolism of choline (via N,N-dimethyl glycine and sarcosine) to the main respiratory chain. The effect of them is to produce reduced ubiquinone ($QH_2$) to join the $QH_2$ produced by Complex I, as described above.

Genetic deficiencies in ETF and ETF-QO are known to be the primary causes of glutaric acidaemia type II, an inborn error characterised clinically by non-ketotic hypoglycaemia and metabolic acidosis. Glutaric acid and sarcosine are found in the urine of glutaric acidaemic type II patients. It was the observation of these same two substances in the urine of patients suffering ifosfamide encephalopathy which was one of the keys to the present invention; the invention may be regarded, in part, as being founded on the discovery that ifosfamide encephalopathy and similar encephalopathies are drug-induced equivalents of the genetic disease. It may be that one of the primary functions of the invention is to restore proper, or at least adequate, electron flow at the site of ETF/ETF-QO.

A further flavoprotein involved in the respiratory or electron transport chain is FAD-containing glycerol phosphate dehydrogenase, which oxidises glycerol phosphate (from cytoplasmic glycolysis) to dihydroxyacetone phosphate while reducing coenzyme Q to join the $QH_2$ pool. Complex II (succinate-ubiquinone oxidoreductase), which dehydrogenates succinic acid to fumaric acid, while reducing coenzyme Q to $QH_2$, also contains flavin as FAD.

Many other important enzymes, in both the mitochondrion and the cytoplasm, are flavoproteins, and their proper functioning may also be disturbed by ifosfamide (or at least its metabolites). It may not matter whether the flavoprotein is covalently or non-covalently bound to its apoprotein; flavin is known to be bound in a variety of different ways and held in different electrostatic microenvironments, so that it may have a variety of different redox potentials in different circumstances.

Chlorethylamine, another metabolite of ifosfamide, would be a substrate for monoamine oxidase, another mitochondrial flavoprotein, by which it would be oxidised to chloracetaldehyde and chloracetic acid, whose toxic effects have already been discussed in detail.

As was mentioned above, ifosfamide is also known to be metabolised into various aldehydes in the liver, namely chloracetaldehyde, acrolein ($CH_2$=CH—CHO), and aldoifosfamide. Acrolein is also a well known metabolite of cyclophosphamide and is extremely toxic to the bladder causing haemorrhagic cystitis. It is postulated that when ifosfamide is administered orally, these aldehyde metabolites super-saturate the available supply of hepatic aldehyde dehydrogenases, thereby depleting NAD stores with a coinciding build-up in NADH levels. Accordingly, without available dehydrogenases, these toxic aldehyde metabolites depart the liver exerting various systemic toxicities, including encephalopathy, in the human body. It may well be that an important function of this invention is simply to prevent the accumulation of toxic aldehyde metabolites, such as chloracetaldehyde, in the liver and thereby preventing exertion of their toxic effects, including encephalopathy, systemically throughout the body.

In sum, it can be seen that there are many vulnerable flavin-containing enzymes and other flavoproteins in the cell, particularly in the mitochondrial membrane, whose proper functioning is vital to the cell. Their prolonged disruption could be fatal.

Methylene blue (3,7-bis(dimethylamino)phenothiazin-5-ium chloride) has the structure

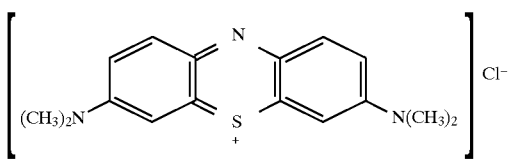

and is able to oxidise a reduced flavin moiety, thus freeing it from being locked in its reduced form. It has been used in an attempt to treat congenital glutaric acidaemic type II (Frerman & Goodman, "Glutaric Acidemia Type II and Defects of the Mitochondrial Respiratory Chain", Chapter 34 in "The Metabolic Basis of Inherited Disease", 6th Edition, McGraw-Hill, 1989 and Harpey et al. *The Lancet*, 1:391 (1986)). Methylene blue is also administered as a means for preventing ethanol-induced hypoglycemia by oxidising NADH to $NAD^+$ and restoring hepatic glucose output depressed by high ethanol consumption. Madison et al., *Diabetes*, 16:252–258 (April, 1967). It is believed that methylene blue is acting in a similar fashion in its prevention and treatment for the onset of ifosfamide encephalopathy.

As discussed previously, after the oral administration of ifosfamide, chloracetaldehyde or other toxic ifosfamide metabolites are formed in the liver. In order for the liver to process these metabolites, various flavin-dependent dehydrogenase enzymes are required. Additionally, since it is believed that ifosfamide saturates the aldehyde dehydrogenase enzymes in the liver thereby lowering the supply of NAD available, encephalopathy results. Methylene blue however, is able to treat as well as prevent this toxicity due to its redox potential. The methylene blue causes NADH to be oxidised to $NAD^+$ thereby simultaneously activating the aldehyde dehydrogenases in the liver. These activated aldehyde dehydrogenase enzymes ultimately break down the ifosfamide metabolites and decrease significantly the levels of circulating ifosfamide metabolites which can cause systemic toxicity.

It is also a proposed that methylene blue is acting as a type of chlorinating agent, chlorinating the toxic ifosfamide metabolites and thereby forming non-toxic metabolites that are excretable in urine. This proposal comes from the identification of three surprising and novel urinary metabolites found among those patients treated with both ifosfamide and methylene blue. These metabolites are 2,2,2-trichlorethanol ($CCl_3CH_2OH$), trichloracetic acid ($CCl_3COOH$), and 3-chlorproprionic acid ($ClCH_2CH_2COOH$). The first two metabolites arise by the dichlorination of chloracetaldehyde. Trichloroethanol in rather large doses is a known sedative compound. The last metabolite, 3-chlorproprionic acid, is believed to be formed by the addition of a chlorine atom to acrolein. It is postulated that when methylene blue is reduced to leucomethylene blue in the human body, that hydrogen peroxide is generated. The hydrogen peroxide is readily able to interact with chloride ions ($Cl^-$) forming hypochloric acid (HOCl). Hypochloric acid is also a powerful chlorinating agent. It is believed that the hypochloric acid formed by the metabolism of methylene blue, sequentially adds two chlorine atoms to the β-carbon of chloracetaldehyde, chlorethanol and chloracetic acid to ultimately yield trichlorinated, non-toxic ifosfamide derivatives. These ifosfamide derivatives are subsequently excreted in the urine. It is also thought the hypochloric acid formed by the metabolism of methylene blue also adds one chlorine atom at the double-bond of acrolein yielding 3-chlorproprionic acid which is also non-toxic to the human body and is readily excreted in urine. Analysis of patient urine substantiates these findings.

It is further believed that methylene blue is preventing the onset of encephalopathy by inhibiting the functioning of plasma amine oxidases. The plasma amine oxidases readily convert 2-chloroethylamine to chloracetaldehyde. Neumann et al., *The Journal of Biological Chemistry*, 260: 6362–6367 (1975). Methylene blue is therefore believed to prevent the accumulation of the various ifosfamide metabolites in the liver by: 1) oxidising reduced flavin moieties hence activating aldehyde dehydrogenase enzymes in the liver; 2) acting as a rapid chlorinating agent; and 3) by inhibiting plasma amine oxidases and thus preventing the conversion of 2-chlorethylamine to chloracetaldehyde. Analysis of patient urine also substantiates the proposal regarding inhibition of plasma amine oxidases.

Other compounds which may be useful in the practice of the invention include riboflavin, other flavins and flavoproteins, phenazine methosulphate, ferricyanides such as sodium ferricyanide, and ubiquinone, as they are able to oxidise reduced flavin in various circumstances. Compounds useful in the invention will generally be supplied in oxidised form, but it may be feasible for them to be administered in reduced form for oxidation by the body's endogenous oxidising agents.

A particularly preferred embodiment of the invention is the use of methylene blue in the preparation of a medicament for preventing or treating ifosfamide encephalopathy. The invention therefore has application in a method of treating or preventing ifosfamide encephalopathy, the method comprising administering to a subject an effective amount of methylene blue. Structural analogues and derivatives of methylene blue in which the redox potential and/or other chemical properties are not significantly disturbed are also useful in this invention and are included within the term "methylene blue" unless the context requires otherwise.

According to a second aspect of the invention, there is provided a product comprising a first compound and a second compound, wherein the first compound is able to oxidise a reduced flavin moiety and wherein the second compound is ifosfamide or another compound which causes toxicity in a manner similar to ifosfamide, as a combined preparation for simultaneous, separate or sequential use in cancer chemotherapy or other therapy involving the second compound. A preferred embodiment of this aspect of the invention provides a product comprising ifosfamide and methylene blue as a combined preparation for simultaneous, separate or sequential use in cancer chemotherapy.

According to a third aspect of the invention, there is provided a pharmaceutical formulation comprising a first compound and a second compound, wherein the first compound is able to oxidise a reduced flavin moiety and wherein the second compound is ifosfamide or another compound which causes toxicity in a manner similar to ifosfamide, and optionally a pharmaceutically acceptable carrier. A preferred embodiment of this aspect of the invention provides a pharmaceutical formulation comprising ifosfamide and methylene blue, and optionally a pharmaceutically acceptable carrier.

In the practice of the preferred embodiment of the invention, in its various aspects, ifosfamide may be administered parenterally (for example by intravenous injection or, more usually, infusion) but is preferably administered orally. Ifosfamide dosages are conventionally measured in terms of grams of drug per square meter of the patient's total body surface area. (The body surface area of a 70 kg adult male is typically about 1.7 $m^2$.) In a four to six day cycle of intravenously administered ifosfamide, a total dosage for treatment of 10 to 18 g/m² may typically be given. The ifosfamide is administered once a day for the duration of the cycle. Orally, ifosfamide has been administered at about 3 to 5 g/m² over a treatment cycle. These dosages are not expected to be limiting on the present invention; indeed, the invention may make it possible for the patient to receive higher doses than has hitherto been considered reasonable. Also, although continuous infusion of ifosfamide has been found to give rise to fewer instances of encephalopathy than injection, it may be that, by means of the present invention, continuous infusion may be dispensed with in a greater number of cases; even if the patient still has to be hospitalised, he may therefore at least be ambulatory. In all cases, the actual dose administered and the method of administration will be at the discretion of the clinical oncologist or other physician.

Ifosfamide therapy is in practice not contemplated without treatment to reduce the severe bladder toxicity of the drug. Mesna (sodium 2-mercaptoethanesulphonate) is usually used for this purpose. Typically, mesna is administered at 60–100% (w/w) of the total dose of ifosfamide. Mesna treatment is usually started with or just before the first dose of ifosfamide, at which time a 20% dose may be given; subsequent doses of 20% may then be given every few hours. Mesna is usually administered by intravenous injection. Oral administration might be preferred, given that the patient may be receiving a variety of other medicaments by injection or infusion, but mesna has a foul taste. If it is given orally, attempts are usually made to disguise the taste, such as by formulating it in a soft drink, such as cola, or something stronger, such as whisky. On oral administration, the mesna dose is usually doubled, to compensate for bioavailability losses.

Other compounds which reduce toxic symptoms of ifosfamide may be administered instead of or as well as mesna. For example, pyritinol, has the following chemical formula:

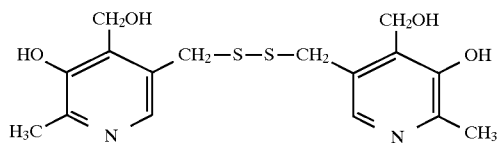

and is the dimer of the thiol analogue of pyridoxine (a derivative of vitamin B₆), and may be used as an ifosfamide detoxificant as it is believed to have a similar action to mesna but is sufficiently lipophilic to cross the blood-brain barrier. The use of pyritinol in reducing ifosfamide (and other phosphoramide, including cyclophosphamide) toxicity forms an independent part of the invention.

According to a fourth aspect of the invention, there is provided the use of pyritinol in the preparation of a medicament for reducing or preventing phosphoramide, particularly ifosfamide or cyclophosphamide, toxicity.

According to a fifth aspect of the invention, there is provided a product comprising pyritinol and a phosphoramide, particularly ifosfamide or cyclophosphamide, as a combined preparation for simultaneous, separate or sequential use in chemotherapy, particularly cancer chemotherapy.

According to a sixth aspect of the invention, there is provided a pharmaceutical formulation comprising pyritinol and a phosphoramide, particularly ifosfamide or cyclophosphamide, and optionally a pharmaceutically acceptable carrier.

It is believed that pyritinol elevates intracellular thiol concentrations thereby detoxifying the chloroethyl metabolites formed by ifosfamide. Pyritinol is metabolised by reduction of its centralised disulfide bond, presumably by glutathione reductase or a similar enzyme using GSH as its cofactor. Pyritinol is also known to be metabolised by S-methylation and S-oxidation into the following metabolites:

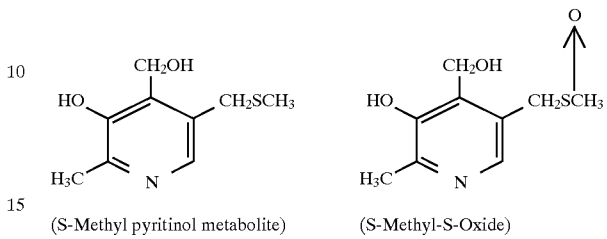

(S-Methyl pyritinol metabolite)    (S-Methyl-S-Oxide)

These metabolites are the excretable forms of pyritinol in urine. In patients not receiving ifosfamide treatment, virtually 100% of pyritinol will be excreted in its metabolised form into the urine. Upon administration of ifosfamide however pyritinol is excreted solely in its unmetabolised non-reduced form. This surprising result further supports the belief that ifosfamide treatment depletes the intracellular stores of free thiols by significantly lowering levels of available NADH and GSH in the respiratory chain. As was previously mentioned, without GSH as a cofactor, glutathione reductase is unable to reduce pyritinol into its metabolised form. It is therefore a further aspect of this invention to use the excretion of unmetabolised pyritinol as a biochemical marker for the onset of encephalopathy upon administration of ifosfamide. It has also been demonstrated that metabolised forms of pyritinol will subsequently be excreted in the urine upon addition of methylene blue, leucomethylene blue or similar compound to the schedule of treatment, further supporting the belief that methylene blue restores mitochondrial functions to normality.

Cytotoxic drugs such as ifosfamide are often given in combination with others. Typical cytotoxic drugs administered in combination with ifosfamide include adriamycin and cisplatin, particularly, but others may be used. Examples include cytosine arabinoside (araC), dacarbazine, epirubicin, VP16, vinca alkaloids such as vincristine and vinblastine, bleomycin, mitomycin C, BCNU, CCNU, 5-fluorouracil and methotrexate. Usual doses and modes of administration of these other cytotoxic drugs would often be used in the practice of the present invention, but again the clinician's judgement would be the final determinant.

Ifosfamide, like many other cytotoxic drugs, causes severe emesis. Consequently, ifosfamide and ifosfamide-containing cocktails, are usually administered in conjunction with an antiemetic. There are various known classes of antiemetics, and the invention is not restricted to the use of any of them. Example s of suitable antiemetics include serotonin (5-HT₃) antagonists and dopamine D₂ antagonists such as metaclopramide. Newer antiemetics include ondansetron, tropizatron and novoban. Parenterally, tropizatron is usually administered as a short intravenous infusion, whereas the others are often given as slow intravenous injections. Orally, antiemetics are generally administered in tablet form.

Ifosfamide is conventionally administered either in saline, fructose or glucose solution. In the present invention, the use of glucose is a preferred solution. The use of fructose is the most preferred solution of the present invention, however, any solution containing a five or six carbon sugar moiety that would act as an energy source such as acetyl glycerol may be used. It is well known that patients with glutaric aciduria type II require the administration of glucose to compensate for derangements in fatty-acid oxidation. The accompanying deficiency of glucoeneogenisis in glutaric aciduria is specifically caused by the absence of electron transferring flavoproteins. As with those patients suffering from glutaric aciduria, it is believed that the co-administration of glucose, and in particular fructose, in ifosfamide patients reduces the body's need for gluconeogenesis. The administration of fructose results in augmented hepatic gluconeogenesis and further enhances the oxidation of NADH to NAD. The reoxidation of NAD is believed a vital step in overcoming the effects of encephalopathy. Additionally or alternatively, acetate generated by the action of glycolysis on glucose may serve to dilute out the chloroacetic acid metabolites of ifosfamide. Fructose may be administered orally at a maximum daily dosage of 300 grams and glucose may be administered orally as a 5% solution with a maximum daily dosage of 100 grams.

It is often the case that patients who are undergoing ifosfamide therapy will be in severe pain because of the tumour or tumours being treated. They may therefore be taking painkillers such as morphine (for example as morphine sulphate tablets) or diacetyl morphine.

In the preferred embodiments of the invention, patients receive methylene blue to counteract encephalopathy induced by ifosfamide. Methylene blue may be administered prophylactically, with the aim of preventing encephalopathy, or therapeutically, to rescue a patient from an encephalopathic episode. The literature dosages of methylene blue, when it is being used as a detoxificant, may be used as a guide to suitable doses for use in the invention: from 2 to 3 mg/kg per 24 hour period may be suitable.

In accordance with the invention, methylene blue may be administered orally or parenterally (for example by intravenous injection). The mode of administration will depend in part on whether methylene blue is being administered prophylactically or therapeutically; normally, oral dosage may be preferred for prophylatic use, but the more rapid onset of action provided by parenteral, particularly intravenous, administration is likely to be more suitable for therapeutic rescue use, not least because the patient's ability to swallow may be impaired during encephalopathy.

For oral dosage, it is considered that from 200 to 400 mg per day is considered safe with 100 mg per day dosage increments to a maximum dosage of 500 mg per day. Caution must be used when administering methylene blue since excessive doses produce high quantities of hydrogen peroxide and may subsequently be chlorinated into hypocloric acid during reduction to its leuco form. As was discussed previously, high levels of hypochloric acid can ultimately produce trichloroethanol, which can cause a sedative effect in high dosages. In practice three or four 50 mg oral doses will usually be given. Methylene blue will usually be orally administered as a pharmacopoeia grade solid (for example to Ph. Eur. and Ph. Helv. VII); hard gelatin capsules provide a suitable means of oral administration.

For intravenous administration, the clinician may administer methylene blue as a 2% w/v solution in water for injections or any other suitable excipient. A 2 ml ampoule would contain 25 mg, so to provide a 50 mg dose three to four time a day the contents of an appropriate number of pairs of ampoules would be used.

The invention has been described in general terms predominantly by reference to the presently perceived preferred embodiments, using ifosfamide and methylene blue or leucomethylene blue. Details of how other embodiments of the invention may be put into practice may be deduced by analogy. It is also to be understood that references made throughout this specification to any theory explaining the results herein described is not to limit the scope of this invention. Preferred embodiments of each aspect of the invention are as for each other aspect, mutatis mutandis.

BRIEF DESCRIPTION OF THE DRAWINGS

The invention will now be illustrated by the following non-limiting examples wherein reference is made to the following figures.

1A) 2,2,2-trichloroethanol (peak 1);

1B) 3-chloroproprionic acid (peak 2);

1C) Trichloroacetic acid (peak 3)

Figure 2A:
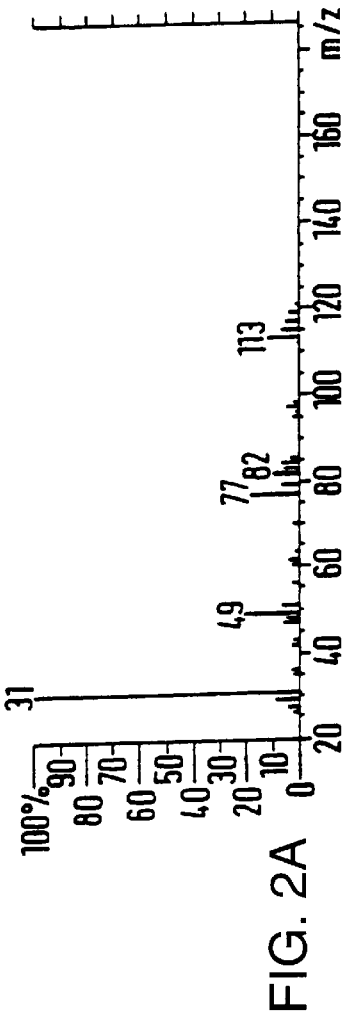
Figure 2B:
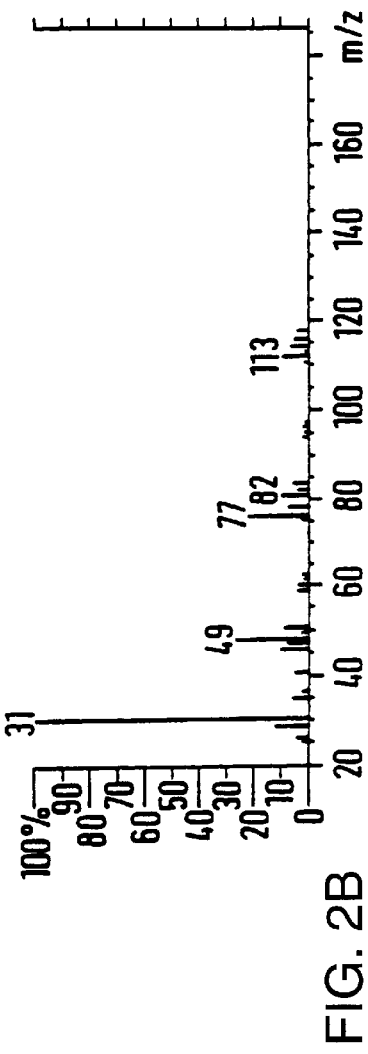
Figure 2B:
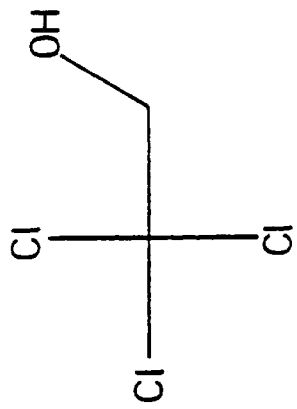

FIG. 2 Reference mass spectra of 2,2,2-Trichloroethanol generated from Fisons Autospec Q MASS LIB GCMS computer reference library at the Department of Organic Chemistry, University of Berne, Switzerland.

Figure 3A:
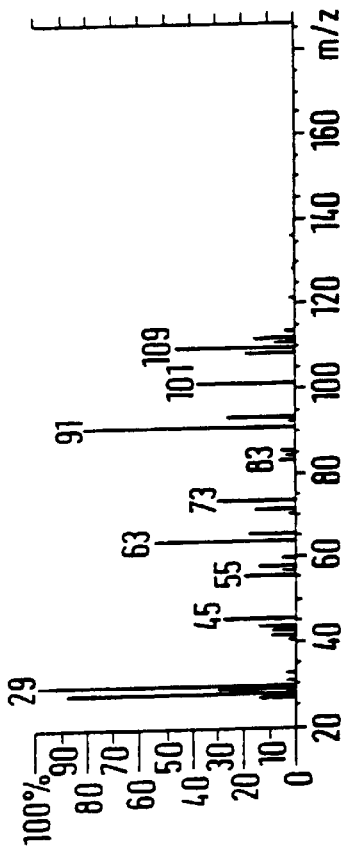
Figure 3B:
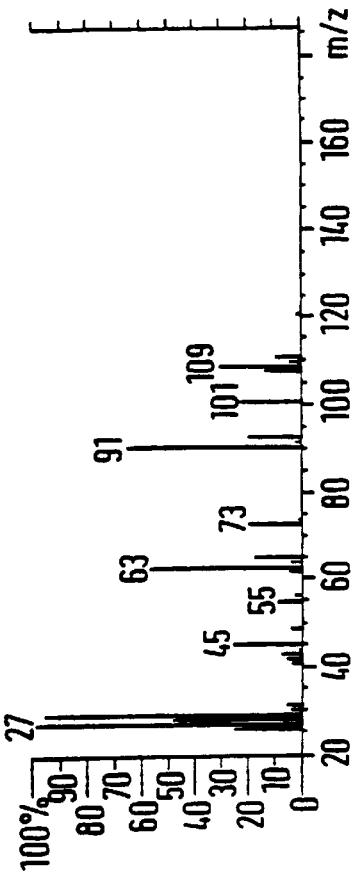

FIG. 3 Reference mass spectra of 3-chloroproprionic acid ethyl ester (3-chloroproprionic acid) generated from Fisons Autospec Q MASS LIB GCMS computer reference library at the Department of Organic Chemistry, University of Berne, Switerland.

Figure 4A:
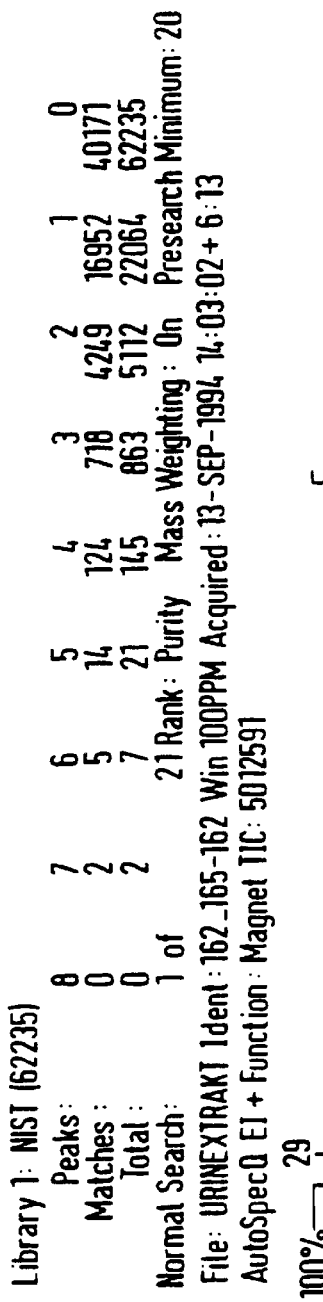
Figure 4B:
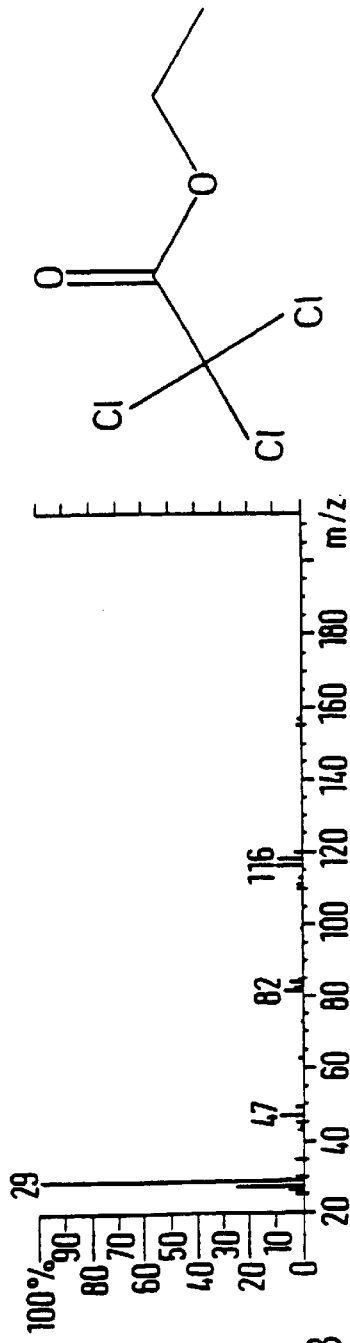
Figure 4B:
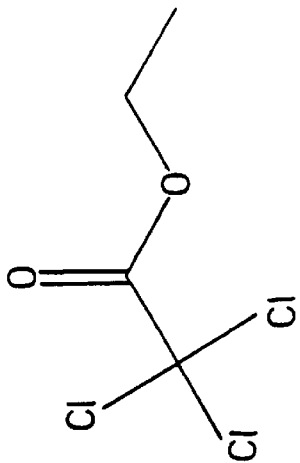

FIG. 4 Reference mass spectra of trichloracetic acid ethyl ester (trichloroacetic acid) generated from Fisons Autospec Q MASS LIB GCMS computer reference library at the Department of Organic Chemistry, University of Berne, Switerland.

EXAMPLES

Example 1

An 18 year old female patient diagnosed with advanced metastatic osteosarcoma began a five day chemotherapy regime. Treatment consisted of a total dosage of 12 g/m$^2$ ifosfamide with 80% (by weight, based on the weight of ifosfamide) mesna and adriamycin (65 mg/m$^2$) divided into two doses. She also received ZOFRAN™ brand ondansetron (antiemetic), 8 mg, by intravenous injection and 200 mg pyritinol three times per day orally. All parenteral medicaments were given in a total of 2 liters 5% glucose solution.

On day three of treatment, the patient had a bad night. She had nightmares and displayed signs of encephalopathy-type hallucinations. The next morning she was still drowsy, disorientated and confused.

50 mg methylene blue, formulated at 2% w/v in water for injections, was administered by slow intravenous injection. After 1 hour, despite continued ifosfamide infusion, she was much calmer, coherent and able to articulate the fearful nature of her hallucinations. The malaise and nausea which she had previously experienced were gone.

About 4 hours later, the 50 mg methylene blue dose was repeated to consolidate the earlier treatment. That night she slept well and was much better the next day. She was still tired, as is usual for ifosfamide-treated patients, but showed no signs of confusion or other symptoms of encephalopathy.

During this cycle of treatment, a nitrobenzyl pyridine (NBP) test of the patient's urine for alkylating metabolites of ifosfamide showed positive. This latter marker indicated that the ifosfamide was active in the patient.

Example 2

After three weeks from the end of the first cycle, the patient who was the subject of Example 1 again was given the same chemotherapeutic regime, except that this time she received 50 mg oral capsules of methylene blue prophylactically three times a day for the full course of treatment. She had no disturbed nights and responded well to the chemotherapy. A lung scan showed that the lung metastases were almost gone, showing the efficacy of the ifosfamide/adriamycin chemotherapy.

An NBP test on her urine showed that alkylating metabolites (presumably of ifosfamide) were present.

Example 3

In 1990, an approximately 50 year old female patient with metastatic leiomyosarcoma was treated for lung metastases with ifosfamide, adriamycin and dacarbazine. She had three cycles of therapy at the time. In the first cycle, she became nervous and restless and exhibited mild encephalopatic signs (such as confusion and amnesia) short of psychosis.

In the second and third cycles, her dose of ifosfamide was 2 g/m$^2$ for three days. In the second cycle, she became psychotic and somnolent. In the third cycle, she became severely psychotic and had hallucinations which continued not only after the end of the cycle but also after discharge from hospital. Apart from the side effects, the chemotherapy was successful, as it resulted in complete remission of the lung metastases.

Between that ifosfamide treatment in 1990 and 1993, she underwent surgery and radiotherapy at various times.

In August 1993, she was referred for ifosfamide treatment again. She had a tumour mass in her lower abdomen and metastases in the lung.

With the following treatment, she received four 50 mg doses of oral methylene blue. Her cytotoxic chemotherapy comprised three 3.2 g doses of ifosfamide (6 g/m$^2$ total dose) split over 3 days. The ifosfamide was administered as a continuous infusion with mesna. She also received 50 mg/m$^2$ adriamycin in two separate doses on days 2 and 3. Additionally, she received pyritinol (200 mg) twice per day on each day of the four day treatment.

The first cycle of treatment has been successfully completed. Despite her history in 1990 of severe encephalopathy, no symptoms of encephalopathy were recorded during treatment. She experienced no malaise and only had one episode of vomiting.

Example 4

A male patient aged 51 years was diagnosed with non small cell lung cancer. He later developed brain, lung and mediastinal and bone metastases. The course of treatment included surgery, irradiation of the brain and chemotherapy. Dosage amounts for chemotherapy were as follows: ifosfamide (1 g/m$^2$) given intravenously for days 1–3; mesna 60% of intravenous ifosfamide dosage plus 800 mg orally twice daily for days 1–3; VP-16 (100 mg) given orally for days 1–8 and methylene blue (50 mg) was administered orally as a loading dose on day 1, with 3×50 mg administered orally on days 1–4. No signs of encephalopathy after four cycles. The patient died 6 months later due to tumour progression.

Example 5

A 50 year old patient (female) was diagnosed with extensive small cell lung cancer with metastases in the abdomen and exhibiting paraneoplastic lambert/Eaton Syndrome. She received six cycles of ifosfamide treatment using the identical dosage requirements as in Example 4. The patient exhibited no signs of encephalopathy and experienced good partial remission and the Lambert/Eaton Syndrome rapidly improved.

Example 6

A 62 year old female patient was diagnosed with non small cell lung cancer with extensive mediastinal lymphnode metastases. She was originally prescribed a course of cisplatinum, VP-16 and velbe. However, no improvements in the disease appeared and the patient suffered from severe nausea, emesis and thrombocytopemia. Oral ifosfamide, VP-16, and methylene blue was then ordered, using the same dosage requirements as described in Example 4 above. Absolutely no signs of encephalopathy were displayed after six cycles of ifosfamide chemotherapy.

Example 7

A 64 year old patient (male) with non small cell lung cancer with involvment of the thoracic wall and retroperitoneal disease began one cycle of ifosfamide/methylene blue chemotherapy. No CNS toxicity was exhibited using dosages as described in Example 4.

Example 8

A male patient, 66 years, was diagnosed with extensive small cell lung cancer with pleural effusion. Patient was prescribed ifosfamide/Vp-16/methylene blue treatment. He received the same dosage amounts as in Examples 4–7, and over a total of six cycles never developed the symptoms associated with encephalopathy. After three cycles with ifosfamide, the patient had partial remission in the primary and lymphnode metastases. After completion of six cycles, the patient had partial remission of the lung, lymphnode and liver metastases.

Example 9

At the request of the inventors, an independent clinical analysis was performed at the Northern Centre for Cancer Treatment, Newcastle Upon Tyne, United Kingdom, on a patient using a combintation of ifosfamide and methylene blue. A female patient aged 35 years was diagnosed with adenocarcinoma of the oesophagus. She began chemotherapeutic treatment and was administered ifosfamide, Mitomycin C, and cisplatin. Following a second cycle of chemotherapy, the patient developed ifosfamide encephalopathy, becoming drowsy and confused. The patient eventually recovered. Upon administration of a third cycle of treatment, the patient was also given a prophylactic dosage of methylene blue. Following this, the patient remained conscious and alert throughout treatment with no further signs of encephalopathy.

Example 10

Figure 1:
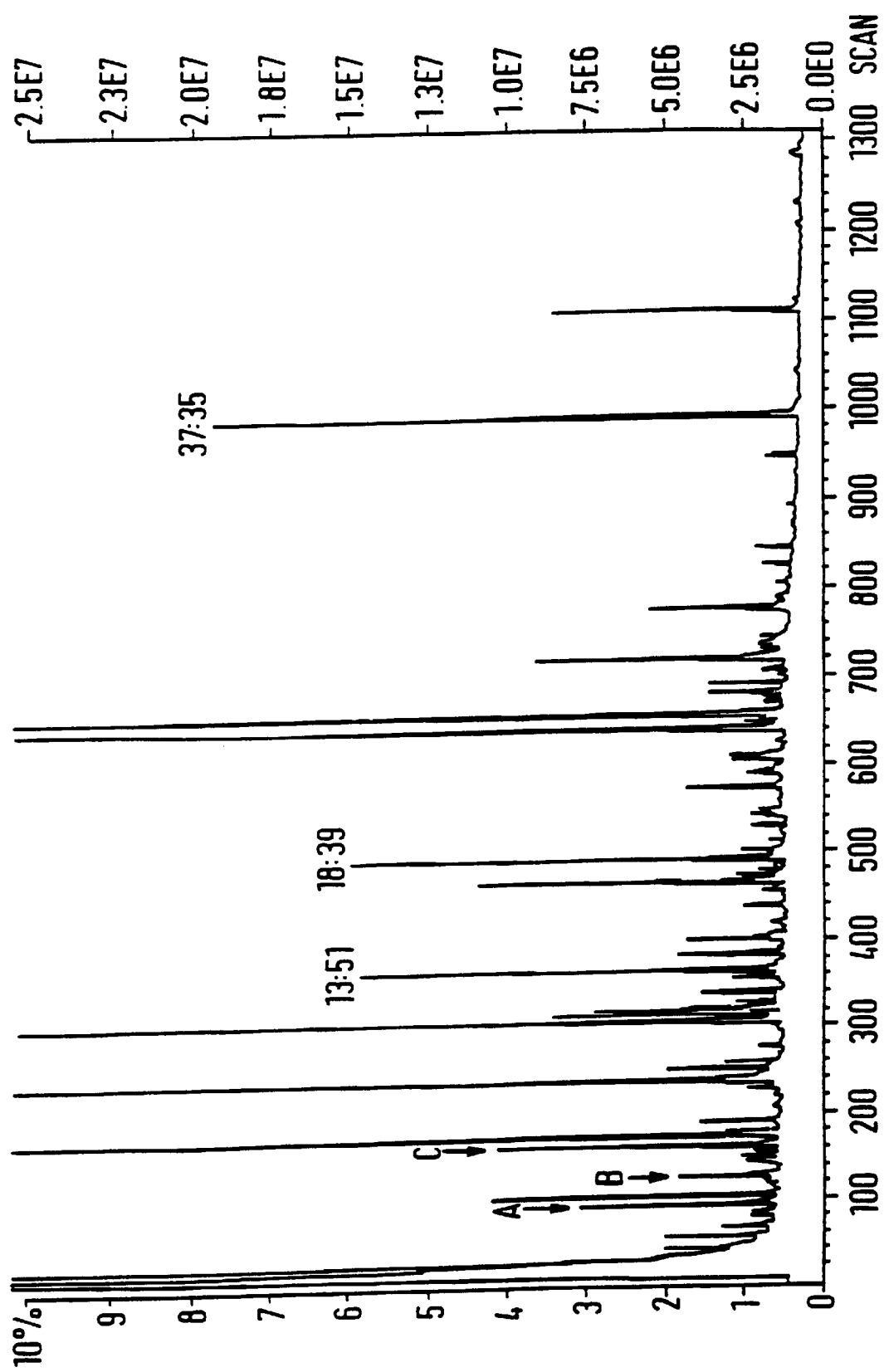
FIG. 1 Gas Chromatography-Mass Spectrometry (GCMS) analysis of urine taken from a patient undergoing chemotherapeutic treatment receiving ifosfamide and methylene blue.

100 ml of urine from a patient having had received methylene blue (300 mg/day) and ifosfamide (3 mg/kg daily) was analysed. The urine was refluxed for 30 minutes with 2M hydrochloric acid in ethanol (50 ml). After sufficient heating, 50 mls each of H$_2$O and 1M hexane were added, the mixture shaken. The organic phase was then reduced to dryness in vacuo on a rotary evaporator. The dry residue was reconstituted in 1M hexane (10 ml) and 1 μl aliquots were submitted to gas chromatography-mass spectrometry analysis (GCMS). A 16 meter OV-17 capillary column was used with a temperature programme set for 40° C. for 1 minute, 5° C. per minute gradient to 250° C. and 250° C. for 10 minutes. Electron impact mass spectra were obtained on the resulting chromatographic peaks of interest (See A, B, and C of FIG. 1). These peaks were analysed through a Fisons Autospec Q MASS LIB GCMS computer library of mass spectra developed by the Department of Organic Chemistry, University of Berne, Switzerland of known organic compounds (FIGS. 2–4). Identity of the three previously unknown eluting peaks were unequivocally identified via computer matching as 2,2,2-trichlorethanal (FIG. 1 A), 3-chloroproprionic acid ethyl ester (FIG. 1 B), and trichloracetic acid ethyl ester (FIG. 1 C).

Example 11

Human or bovine plasma (2.0 ml) containing 2-chlorethylamine (100 μg/ml) was incubated in a shaking water bath at 36° C. for 1 hour. Aliquots (5 μl) were directly injected in to a Tenax packed gas chromatographic column maintained at 120° C. in a Perkin Elmer 3920B gas chromatograph. The product of 2-chlorethylamine oxidation by plasma amine oxidase, 2-chloracetaldehyde, was eluted at 9 minutes retention time. External calibration curves were used to determine concentrations of resulting chloracetaldehyde. Similar experiments in which methylene blue (50 μM) was also added showed an inhibition of plasma amine oxidase by methylene blue of 80%. The methylene blue is thus able to reduce the formation of chloracetaldehyde from 2-chlorethylamine by the plasma to 20% of that observed in the absence of methylene blue.

While we have herein described a number of embodiments of this invention, it is apparent that the basic constructions can be altered to provide other embodiments which utilise the methods of this invention. Therefore, it will be appreciated that the scope of this invention is defined by the claims appended hereto rather than by the specific embodiments which have been presented herein by way of example.

What is claimed is:

1. A method of treating or preventing toxicity caused by ifosfamide, the method comprising administering to a subject in need thereof an effective amount of a compound which is able to oxidize a reduced flavin moiety, wherein the compound is methylene blue.

2. A method of treating or preventing ifosfamide encephalopathy, the method comprising administering to a subject in need thereof an effective amount of methylene blue.

3. A method as claimed in claim 2, comprising administering at least 50 mg methylene blue.

4. A method as claimed in claim 3, comprising administering from 200 to 400 mg methylene blue per day.

5. A method as claimed in claim 4, comprising administering 300 mg methylene blue per day.

6. A method as claimed in claim 2, which further comprises administering fructose.

7. A method as claimed in claim 2, which further comprises administering glucose.

* * * * *